United States Patent
Nardini et al.

(10) Patent No.: US 8,932,336 B2
(45) Date of Patent: Jan. 13, 2015

(54) CABLE TIE L-PIN

(75) Inventors: Reto Nardini, Oberdorf (CH); Dieter Schmidli, Oberdorf (CH); Bruno Laeng, Oberdorf (CH)

(73) Assignee: DePuy Synthes Products, LLC, Raynham, MA (US)

( * ) Notice: Subject to any disclaimer, the term of this patent is extended or adjusted under 35 U.S.C. 154(b) by 177 days.

(21) Appl. No.: 13/409,788

(22) Filed: Mar. 1, 2012

(65) Prior Publication Data

US 2013/0060290 A1   Mar. 7, 2013

Related U.S. Application Data

(60) Provisional application No. 61/475,044, filed on Apr. 13, 2011.

(51) Int. Cl.

| | | |
|---|---|---|
| *A61B 17/04* | (2006.01) | |
| *A61B 17/84* | (2006.01) | |
| *A61F 2/08* | (2006.01) | |
| *A61B 17/86* | (2006.01) | |
| *A61B 17/08* | (2006.01) | |
| *A61D 1/00* | (2006.01) | |
| *A61B 17/68* | (2006.01) | |
| *A61B 17/00* | (2006.01) | |
| *A61B 17/80* | (2006.01) | |

(52) U.S. Cl.
CPC ............. *A61B 17/683* (2013.01); *A61B 17/842* (2013.01); *A61B 17/844* (2013.01); *A61B 2017/005* (2013.01); *A61B 2017/00955* (2013.01); *A61B 17/80* (2013.01)
USPC ............................. 606/300; 606/303; 606/217

(58) Field of Classification Search
USPC ............ 606/151, 217, 232, 330, 78, 303, 310
See application file for complete search history.

(56) References Cited

U.S. PATENT DOCUMENTS

| | | | | |
|---|---|---|---|---|
| 5,735,875 | A | * | 4/1998 | Bonutti et al. ................ 606/232 |
| 6,620,185 | B1 | * | 9/2003 | Harvie et al. ................. 606/232 |
| 2006/0282105 | A1 | * | 12/2006 | Ford et al. ..................... 606/151 |
| 2007/0270833 | A1 | * | 11/2007 | Bonutti et al. .................. 606/61 |

FOREIGN PATENT DOCUMENTS

| | | |
|---|---|---|
| EP | 1 920 721 | 5/2008 |
| WO | 02/09602 | 2/2002 |

* cited by examiner

*Primary Examiner* — David Bates
(74) *Attorney, Agent, or Firm* — Baker & Hostetler LLP

(57) ABSTRACT

A device for treating a bone includes (a) an elongate body sized and shaped for insertion into a bone and extending longitudinally from a proximal end to a distal end, the elongate body including a channel extending therethrough and a coating along an outer surface thereof, the coating adapted to absorb a selected frequency of light such that, when the selected frequency of light is applied thereto, portions of the coating melt to form a mass; and (b) a first anchor member slidably mountable over the elongate body and movable therealong from a first position at the proximal end of the elongate body to a second position adjacent a bone into which the elongate body has been inserted to cooperate with the mass to fix the elongate body to the bone.

29 Claims, 6 Drawing Sheets

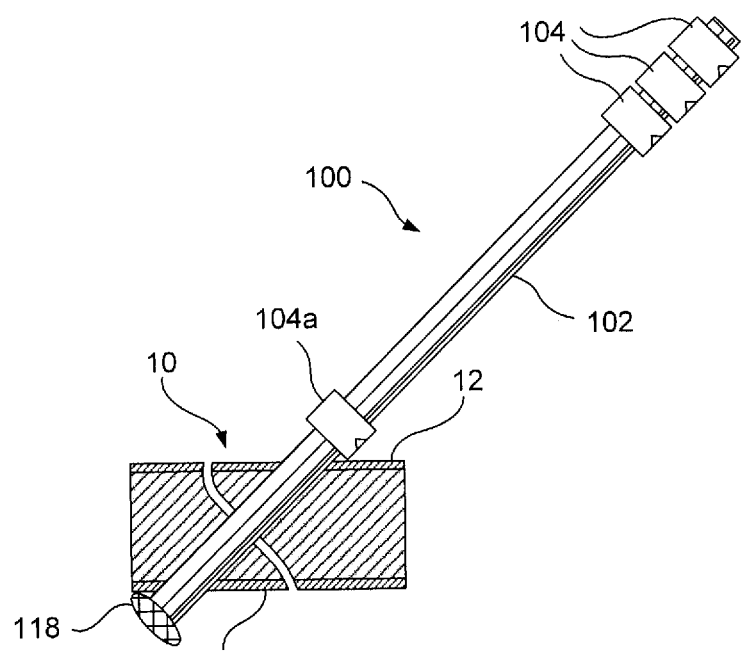
F I G. 7
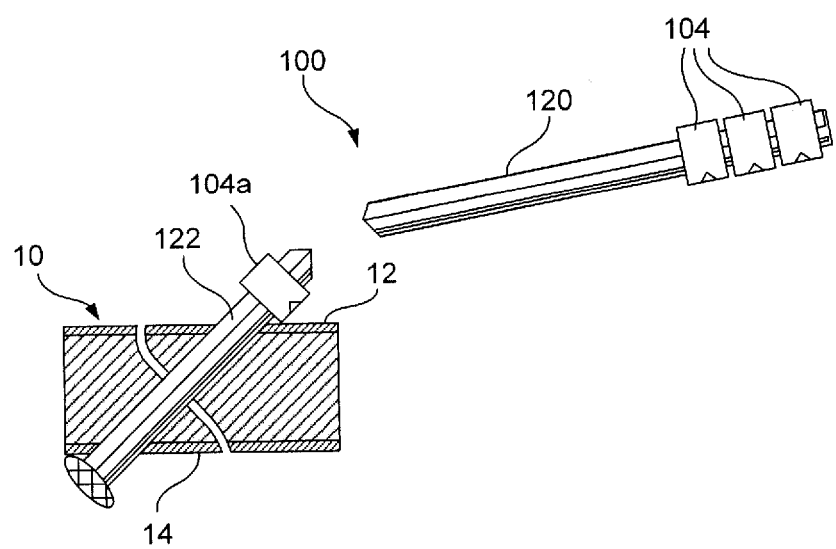
F I G. 8

CABLE TIE L-PIN

PRIORITY CLAIM

The present application claims priority to U.S. Provisional Application Ser. No. 61/475,044 filed on Apr. 13, 2011 and entitled "Cable Tie L-Pin," the entire disclosure of which is incorporated herein by reference.

FIELD OF THE INVENTION

The present invention relates to devices for treating fractures and, in particular, relates an implant for fixing fractures.

BACKGROUND

Fractured bones are often fixed using bone fixation elements such as, for example, bone screws. A length of a bone screw selected for use in a particular procedure is generally based on a number of different factors such as, for example, a size of the bone to be fixed, the location on the bone to be fixed, and a desired angle of insertion of the bone screw. When standard bone screws are applied across a fracture, the threading pulls both fragments of bone in the same direction frustrating attempts to compress the fracture. To achieve compression in this case, a shaft screw is required so that the threading will engage only the fragment of bone on the far side of the fracture. All of these options require specialized screws in a variety of lengths and configurations increasing the materials required for these procedures. Further, bone screws often disengage from the driver complicating these procedures.

SUMMARY OF THE INVENTION

The present invention relates to a device for treating a bone, comprising an elongate body sized and shaped for insertion into a bone and extending longitudinally from a proximal end to a distal end, the elongate body including a channel extending therethrough and a coating along an outer surface thereof, the coating adapted to absorb a selected frequency of light such that, when the selected frequency of light is applied thereto, portions of the coating melt to form a mass and a first anchor member slidably mountable over the elongate body and movable therealong from a first position at the proximal end of the elongate body to a second position adjacent a bone into which the elongate body has been inserted to cooperate with the mass to fix the elongate body to the bone.

BRIEF DESCRIPTION OF THE DRAWINGS

FIG. 7 shows a side view of a repositioned cable tie head ff the device of FIG. 1;

FIG. 8 shows a side view of a remaining portion cut off from an implanted portion of the device of FIG. 1;

DETAILED DESCRIPTION

Figure 1:
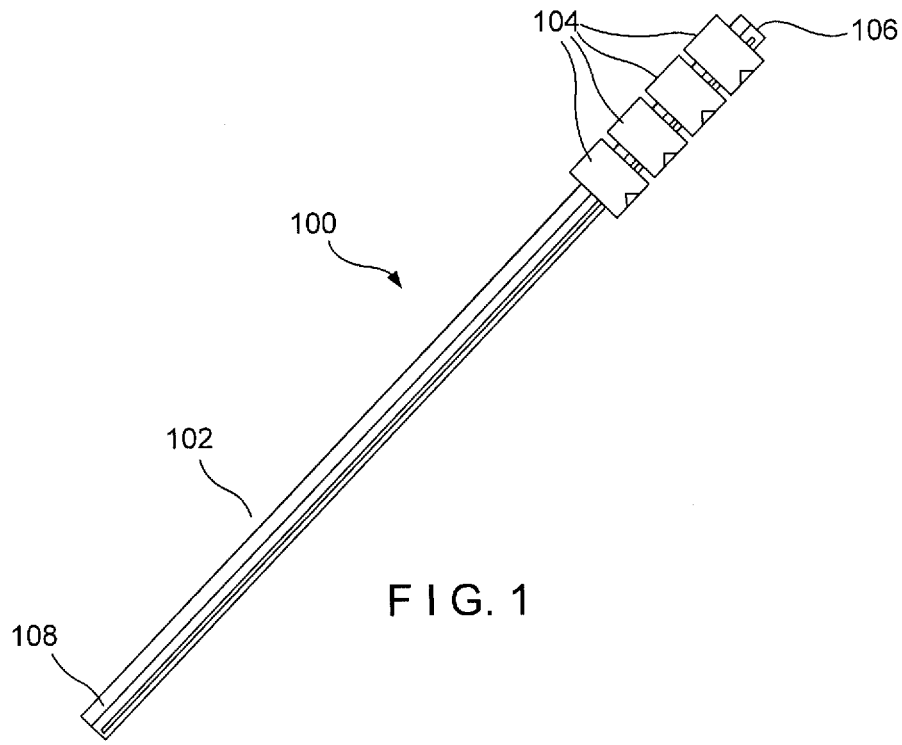
FIG. 1 shows a side view of a device according to an exemplary embodiment of the present invention.

The present invention may be further understood with reference to the following description and the appended drawings, wherein like elements are referred to with the same reference numerals. The present invention relates to devices for treating fractures and, in particular, relates an implant for fixing fractures. Exemplary embodiments of the present invention describe a device including laser pin (L-pin) technology permitting portions of the device to be melted to hold it in place. For example, a distal end of the device may expand radially when melted to anchor the device within or against the bone while a cable tie mechanism is slid proximally along the device to apply compression across the fracture. It should be noted that the terms "proximal" and "distal" as used herein, are intended to refer to a direction toward (proximal) and away from (distal) a user of the device.

As shown in FIGS. 1-9, a device 100 according to an exemplary embodiment of the present invention comprises a body 102 sized and shaped for insertion into a fractured bone 10 and a plurality of anchor members 104 coupled thereto. The anchor members may be cable tie heads 104 which are pre-assembled along a proximal end 106 of the body 102 or mounted thereover during a surgical procedure. The body 102 may be inserted through the bone 10 and a distal end 108 thereof melted using L-pin technology. One cable tie head 104 may then be slid to a desired position along the body 102 adjacent an exterior of a near cortex 12 of the bone 10. A remaining portion of the body 102 may then be cut off proximally of the cable tie head 104 adjacent the bone 10 such that the remaining portion of the body 102 may be reused along with the remaining cable tie heads 104.

Figure 2:
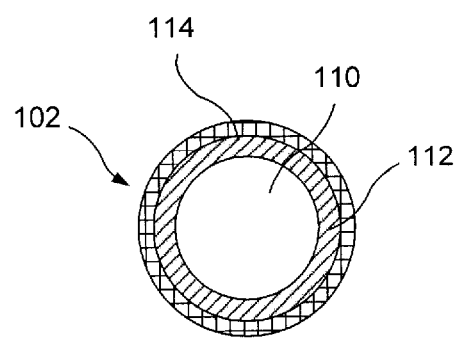
FIG. 2 shows a cross sectional view of a body of the device of FIG. 1.

As shown in FIGS. 1-2, the body 102 extends longitudinally from a proximal end 106 to a distal end 108 and includes a channel 110 extending therethrough. In one exemplary embodiment, the body 102 is substantially tubular with a diameter ranging from between 2 mm and 5 mm. It will be understood by those of skill in the art, however, that the body 102 may be any of a variety of shapes and sizes so long as the body 102 is configured for insertion through or into a portion of bone 10. In one use, the body 102 may be inserted into the bone 10 until the distal end 108 extends distally past a far cortex 14 of the bone 10. The channel 110 is sized and shaped to receive a laser fiber 116 or other laser device therein. The body 102 may be formed of, for example, a metallic core 112 coated with a thermoplastic polymer 114 including a pigment colored to absorb light of the wavelength produced by a laser to be used therewith. In an exemplary embodiment, the thermoplastic polymer coating 114 may extend around the entire exterior surface of the core 112. In an alternate embodiment, the thermoplastic polymer coating 114 may be applied over one or more portions of the core 112 while uncoated portions of the core 112 or portions coated with a clear polymer (or a polymer otherwise unaffected by the laser light) will not be melted when laser light is applied thereto.

The laser fiber 116 emits laser light radially from a distal tip thereof. Thus, when the laser fiber 116 is inserted into the channel 110 and is activated, the laser light at the distal tip melts the thermoplastic polymer 114 at the distal end 108 of the body 102. In particular, the colored pigment within the thermoplastic polymer coating 114 at the distal end 108 absorbs the laser energy, melting the polymer to form a mass 118 which hardens in an expanded shape as the mass 118 cools. Thus, the mass 118 prevents the distal end 108 of the body 102 from being moved proximally back into the bone 10.

One or more cable head tie heads 104 may be positioned along the proximal end 106 of the body 102 and individually movable therealong. Once the body 102 has been positioned in the bone 10 as desired and the distal end 108 has been melted to form the mass 118, a distal-most one of the cable tie heads 104*a* may be moved along the body 102 adjacent the near cortex 12 at a desired position along the body 102 to apply compression to the bone 10. The distal-most cable tie head 104*a* may be, for example, crushed over the body 102 to fix the distal-most cable tie head 104*a* to the body 102 at the desired position. A remaining length 120 of the body 102 extending proximally from the cable tie head 104*a* is then cut off and the distal-most cable tie head 104*a* adjacent the bone 10 is tightened to compress the fracture of the bone 10. In particular, the cable tie head 104*a* may be tightened by moving the distal-most cable tie head 104*a* distally along an implanted portion 122 of the body 102 compressing the fractured bone 10. The cable tie head 104*a* may be prevented from rotating about the body 102 during tightening of the distal-most cable tie head 104*a* via, for example, keyed portions of the body 102 and the cable tie head 104. For example, in one embodiment, the body 102 may have a non-circular cross section corresponding to a non-circular opening extending through the cable tie head 104. In another embodiment, the body 102 may include a teethed extending about an exterior surface thereof. Thus, once the distal-most cable tie head 104*a* is crushed thereover, an inner surface of the cable tie head 104*a* will engage the toothed surface preventing rotation of the cable tie head 104*a* relative to the body 102.

In a further embodiment, the body 102 has a thread along its length. The distal-most cable tie head 104*a* is advanced over the thread to apply an initial compression similarly to the other embodiments. The cable tie head 104*a* is then rotated about the thread to achieve a final compression, which can be to apply either more or less compression by moving the cable tie head 104*a* proximally or distally relative to the body. It is of course possible that the rotation can also be used to remove the cable tie head 104*a* completely from the body 102. After the cable tie head 104*a* is adjusted to a desired position, it may be, for example, crushed over the body 102 to fix it at that position The remaining length 120 and the remaining cable tie heads 104 may be reused. In one embodiment, the device includes four cable tie heads 104. It will be understood by those of skill in the art, however, that the device 100 may include any number of cable tie heads 104 depending on a number of times that the device 100 may be used. Similarly, a length of the body 102 may also vary depending on the number of times that the device 100 may be used. For example, the body 102 may have a length ranging from between 20 to 240 mm. Thus, the number of cable tie heads 104 may also correspond to the length of the body 102. It will be understood by those of skill in the art that although a plurality of cable tie heads 104 is specifically described, the device 100 may include one cable tie head 104.

Figure 3:
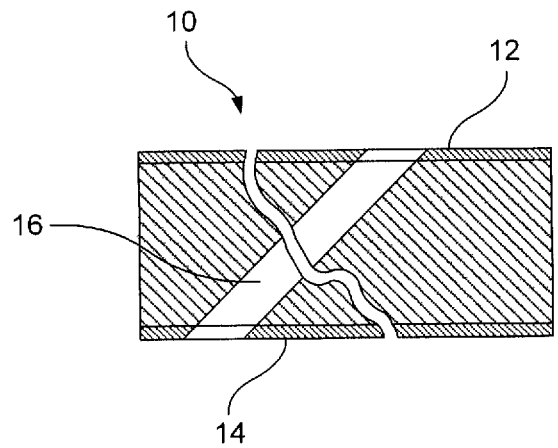
FIG. 3 shows a side view of a bone in which fractured portions are reduced and a hole drilled therethrough to accommodate the device of FIG. 1.
Figure 4:
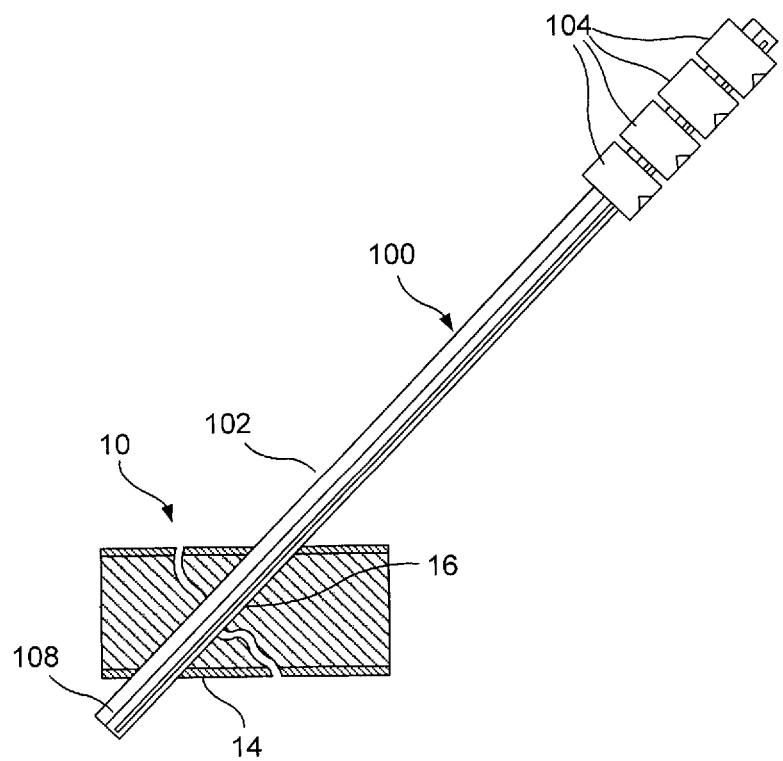
FIG. 4 shows a side view of the device of FIG. 1 inserted into the bone of FIG. 2.
Figure 5:
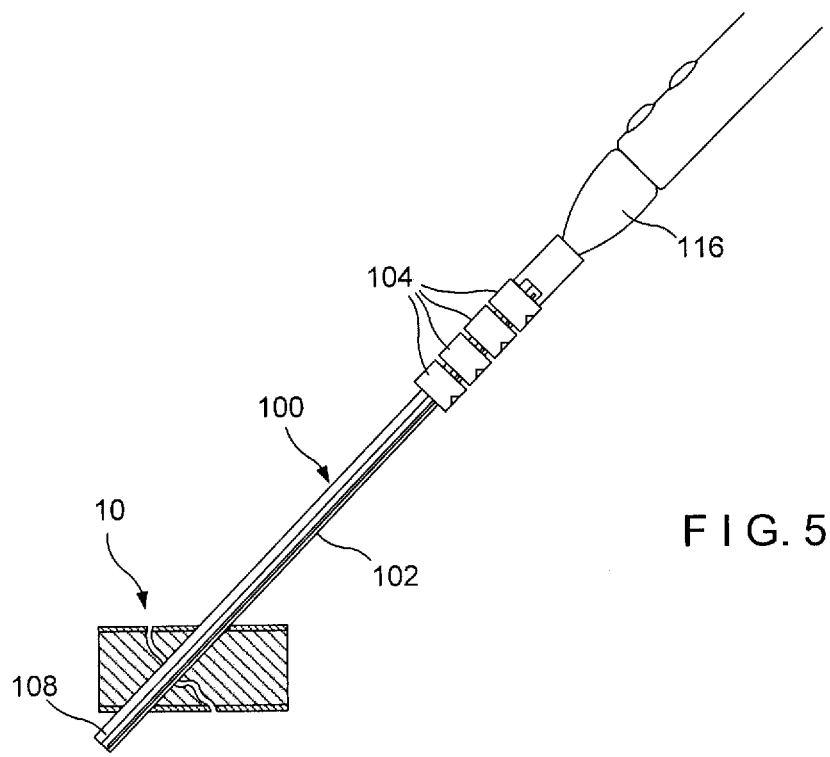
FIG. 5 shows a side view of a laser inserted into the device of FIG. 1.
Figure 6:
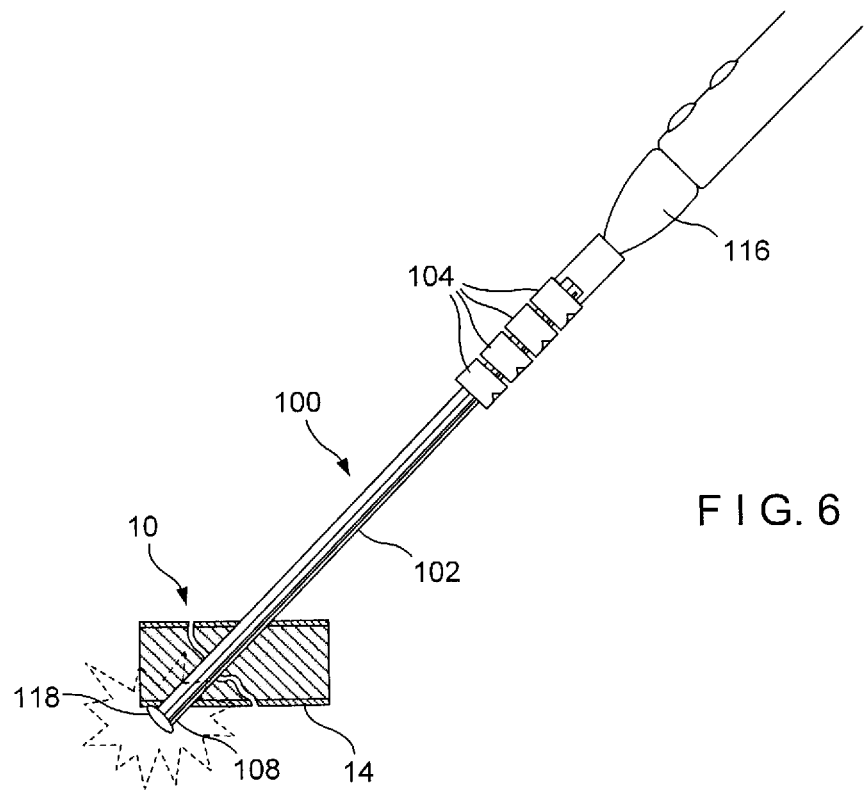
FIG. 6 shows a side view of the laser melting a distal end of the device of FIG. 1.

According to an exemplary surgical technique using the device 100, fractured portions of a bone 10 are reduced and a hole 16 is drilled therethrough along a desired path over which the body 102 is to be inserted into the bone 10 to fix the fractured portions, as shown in FIG. 3. The body 102 may then be inserted through the drilled hole 16, as shown in FIG. 4, until the distal end 108 of the device extends distally past a far cortex 14 (e.g., past an exterior surface of the far cortex 14) of the bone 10. As shown in FIG. 5, the laser 116 is then inserted through the channel 110 until a distal tip thereof is positioned radially within the distal end 108 of the body 102 and the laser 116 is activated to melt the distal end 108 forming the mass 118, as shown in FIG. 6. As described above, the mass 118 prevents the distal end 108 of the body 102 from being drawn proximally back into the bone 10.

Figure 9:
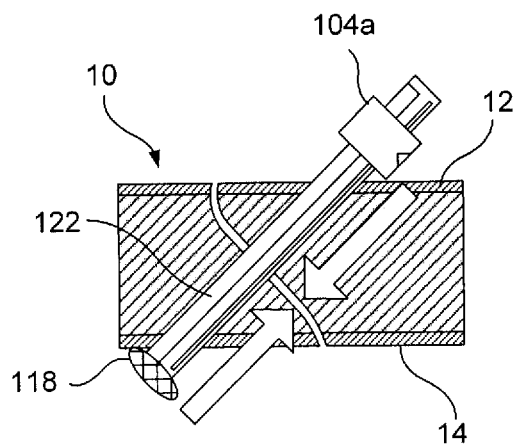
FIG. 9 shows a side view of the implanted portion of the device of FIG. 1.

The laser 116 is then removed from the device 100 and the distal-most cable tie head 104*a* is slid distally along the body 102 until it abuts an exterior surface of a near cortex 12 of the bone 10, as shown in FIG. 7. Once the distal-most cable tie head 104*a* has been positioned along the body 102, as desired, a remaining length 120 of the body 102 extending proximally from the cable tie head 104 is severed from the implanted portion 122, as shown in FIG. 8. The remaining cable tie heads 104 remain positioned along the proximal end 106 of the remaining length 120. The distal-most cable tie head 104*a* is then tightened, if desired, to achieve a desired compression of the bone 10. Since the mass 118 abuts the far cortex 14, tightening the distal-most cable tie head 104 (i.e., moving the distal-most cable tie head 104*a* distally relative to the implanted portion 122) compresses the bone 10, as shown in FIG. 9.

Figure 10:
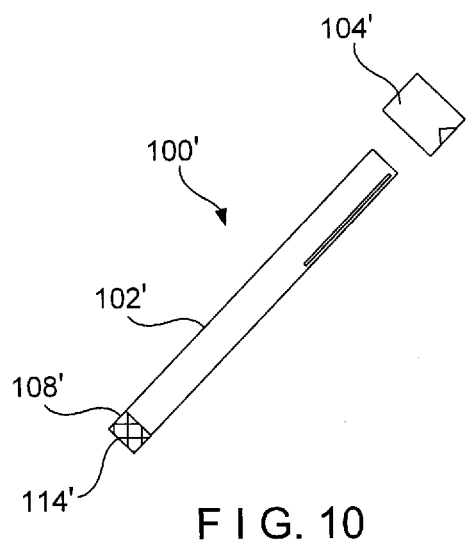
FIG. 10 shows a side view of a device according to an alternate embodiment of the present invention.

The remaining length 120 of the body 102 and the remaining cable tie heads 104 may be reused to fix other bones or other portions of the bone 10. The remaining length 120 and cable tie heads 104 may be used in the same manner, as described above, until a remaining length is insufficient to compress a bone and/or no more cable tie heads 104 remain. In an alternative embodiment, as shown in FIG. 10, a device 100' may be substantially similar to the device 100, described above, but may be configured for a single use. For example, a length of a body 102' may be selected to provide for a single compression of a bone and the device 100' may include a single cable tie head 104'. In addition, since the device 100' is suited for a single use, the body 102' may include a thermoplastic coating 114' along a distal end 108' only. It will be understood by those of skill in the art, however, that the thermoplastic coating 114' may extend along any portion or an entire exterior surface of the body 102'. For example, portions of the body 102' may be coated with a clear polymer (or a polymer otherwise unaffected by the laser light) to direct laser light to the distal end 108' such that a colored pigment within the thermoplastic coating 114' along the distal end 108' absorbs the laser energy, melting the polymer at the distal end 108' to form a mass which hardens in an expanded shape. The device 100' may be used in a manner substantially similar to the surgical technique described above. Specifically, the body 102' is inserted through a bone such that the distal end 108' extends distally beyond a far cortex thereof. The laser is then inserted through the body 102' and energy is applied thereto such that the pigmented polymer coating along the distal end 108' is melted to form a mass. The laser may then be removed and the cable tie head 104' moved distally along the body 102' to compress the bone, as desired. It will be understood by those of skill in the art, however, that the device 100' may not require a remaining length of the body 102' to be cut off from an implanted portion of the body 102' since a length of the body 102' may be specifically selected for a single use.

Alternatively, rather than being coated with the polymer material, the body 102' may be formed of a clear polymer material such as for example, polylactide or polycaprolactone, which may be either oriented or non-oriented. The polymer may include an additional expanding substance such as, for example, water in bubbles or Natron. The distal end 108' may include a laser absorbent material such as a colored pigment such that when the laser is applied to the body 102', the pigmented portion of the polymer is melted to form a mass. Since the body 102' is formed of the clear polymer material, which is unaffected by the laser energy, a laser applied to the body 102' will be directed to the pigmented portion at the distal end 108' such that the body 102' does not require a channel extending therethrough to receive the laser device. The colored pigment may be, for example, Indocyanine green or Blue No. 9.

Figure 11:
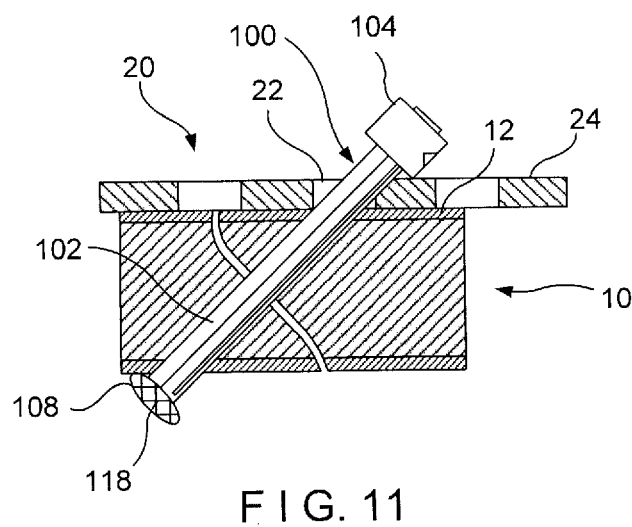
FIG. 11 shows a side view of the device of FIG. 1 used in conjunction with a bone plate.

According to a further exemplary embodiment, as shown in FIG. 11, the device 100 may be used in conjunction with a bone plate 20. The bone plate 20 is positioned along the near cortex 12 of the bone 10 in which fractured portions are reduced, and the device 100 is used in a manner substantially similar to the surgical technique described above. In particular, a hole may be drilled through an opening 22 of the bone plate 20 and the body 102 inserted therein, as described above. The distal end 108 is similarly melted to a mass 118 and the cable tie head 104 is moved proximally along the body 102. Rather than abutting a near cortex of the bone 10, however, the cable tie head 104 abuts a surface 24 of the bone plate 20. The cable tie head 104 may be similarly tightened to compress the fractured bone 10.

Figure 12:
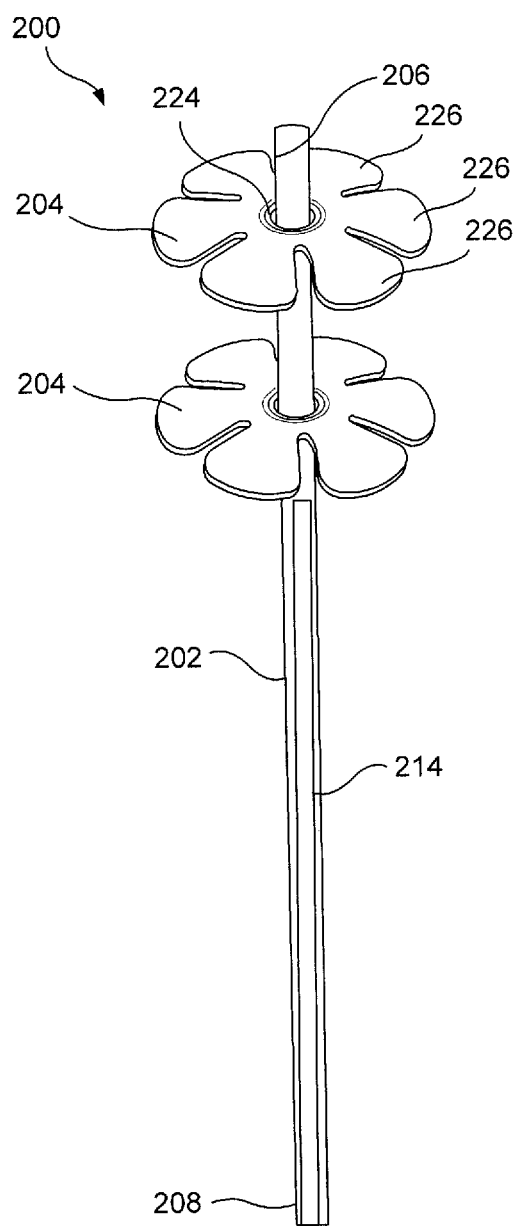
FIG. 12 shows a perspective view of a device according to another exemplary embodiment of the present invention.

As shown in FIG. 12, a device 200 may be substantially similar to the device 100, as described above, comprising a body 202 and a plurality of anchor members 204 coupled thereto and slidable therealong. Similarly to the device 100, the body 202 extends longitudinally from a proximal end 206 to a distal end 209 and includes a thermoplastic polymer coating 214 along a length thereof such that a laser device may melt the distal end 208, as described above. The anchor member 204, however, is not fixed to the body 202 at a desired position therealong via a cable tie mechanism, as described above in regard to the device 100. Rather, the anchor members 204 may be welded to the body 202 at a desired position therealong by melting the thermoplastic polymer coating 214 at the desired position.

The anchor member 204 may include an opening 224 extending therethrough for accommodating the body 202 and a plurality of radially extending flaps 226. The flaps 226 may be bent relative to one another such that when the anchor member 204 is positioned along a near cortex of the bone, the flaps 226 may be deformed to conform to a surface the of the near cortex. Although the anchor member 204 is specifically shown as a substantially planar element including radially extending flaps 226, it will be understood by those of skill in the art that the anchor member 204 may have any of a variety of shapes and sizes so long as the anchor member 204 is formed of a material that may be welded to the body 202 by melting the thermoplastic polymer coating 214 at a position corresponding to a position of the anchor member 204. For example, the anchor member 204 may be formed of a metal material.

The device 200 may be utilized in a manner substantially similar to the exemplary surgical technique described above with respect to the device 100. In particular, the body 202 is inserted into a bone until the distal end 208 extends distally beyond a far cortex thereof. A laser device is then inserted through a channel extending through the body 202 until a distal end of the laser device is positioned radially within the distal end 208 such that the distal end 208 may be melted to form a mass. Once the mass has been formed at the distal end 208, a distal-most one of the anchor members 204 is moved distally along the body 202 until it is pressed against the near cortex of the bone in a desired position along the body 202. The distal-most anchor member 204 should be pressed against the near cortex while the mass at the distal end 208 is pressed against the far cortex. The distal end of the laser device is positioned radially within the body 202 at the desired position corresponding to the distal-most anchor member 204. The laser device is activated to melt the thermoplastic polymer 214 at the desired position such that the anchor member 204 is welded thereto. A remaining length of the body 202 extending proximally from the distal-most anchor member 204 may be severed from an implanted portion thereof such that the remaining length may be reused to fix other bones or other portions of the bone, as discussed above in regard to the device 100.

It will be understood by those of skill in the art that the device 200 may include any number of anchor members 204 depending on a desired number of uses of the device 200 and a length of the elongate body 202 may be similarly selected for the desired number of uses. Alternatively, the device 200 may be configured for a single use, including a single anchor member 204 and a body 202 having a corresponding length.

It will be apparent to those skilled in the art that various modifications and variations can be made in the structure and the methodology of the present invention, without departing from the spirit or scope of the invention. For example, in any of the above described methods, the distal end of the body 102 may be located within a bone abutting an internal structure thereof. Thus, it is intended that the present invention cover the modifications and variations of this invention provided that they come within the scope of the appended claims and their equivalents.

What is claimed is:

1. A device for treating a bone, comprising:
   an elongate body sized and shaped for insertion into an aperture of a bone and extending longitudinally from a proximal end to a distal end, the elongate body including a channel extending therethrough and a coating along an outer surface of the elongate body, the coating adapted to absorb a selected frequency of light such that, when the selected frequency of light is applied thereto, portions of the coating at the distal end melt to form a mass, wherein the distal end has an initial cross-sectional dimension less than that of the aperture prior to application of the selected frequency, and the mass has a cross-sectional dimension greater than both the initial cross-sectional dimension and further greater than that of the aperture; and
   a first anchor member slidably mountable over the elongate body and movable therealong from a first position at the proximal end of the elongate body to a second position adjacent a bone into which the elongate body has been inserted to cooperate with the mass to fix the elongate body to the bone,
   wherein a proximal portion of the elongate body is severable from a first implanted portion extending from the distal end into the first anchor member, the device including a second anchor member, wherein a length of the proximal portion of the elongate body is sufficient to form a second implanted portion.

2. The device of claim 1, wherein the coating is formed of a thermoplastic polymer including a pigment absorbing the selected frequency of light.

3. The device of claim 1, further comprising a third anchor member, wherein a length of the proximal portion of the elongate body is sufficient to form a third implanted portion.

4. The device of claim 1, wherein the coating extends along an entire outer surface of the elongate body.

5. The device of claim 1, wherein the coating surrounds the distal end of the elongate body.

6. The device of claim 1, wherein the first anchor member includes a plurality of deformable flaps extending radially therefrom.

7. The device of claim 1, wherein the portions of the coating at the proximal end of the elongate body do not deform when the selected frequency of light is applied to the distal end.

8. The device of claim 1, further comprising a plurality of anchor members slidably mountable over the elongate body, wherein the plurality of anchor members includes the first anchor member, and the first anchor member is movable along the elongate body away from all others of the plurality of anchor members from the first position to the second position.

9. The device of claim 1, further comprising a light fiber sized and shaped for insertion into the channel of the elongate body and emitting a light from a distal tip thereof.

10. The device of claim 9, wherein the light fiber emits the light at the selected frequency of light so as to form the mass.

11. A system for treating a bone, comprising:
a bone fixation device including:
an elongate body sized and shaped for insertion into a bone and extending longitudinally from a proximal end to a distal end, the elongate body including a channel extending therethrough and a coating along an outer surface of the elongate body, the coating adapted to absorb a selected frequency of light such that, when the selected frequency of light is applied thereto, portions of the coating melt at the distal end to form a mass, wherein the distal end has an initial cross-sectional dimension prior to absorption of the selected frequency of light by the coating, and the mass has a second cross-sectional dimension greater than the initial cross-sectional dimension; and
a first anchor member slidably mountable over the elongate body and movable therealong from a first position at the proximal end of the elongate body to a second position adjacent a bone into which the elongate body has been inserted to cooperate with the mass to fix the elongate body to the bone; and
a light fiber sized and shaped for insertion into the channel of the elongate body and emitting a light from a distal tip thereof.

12. The system of claim 11, further comprising a bone plate including an opening sized and shaped to receive the elongate body therethrough.

13. The system of claim 11, wherein the coating is formed of a thermoplastic polymer including a pigment absorbing the selected frequency of light.

14. The system of claim 11, wherein a proximal portion of the elongate body is severable from a first implanted portion extending from the distal end into the first anchor member, the device including a second anchor member, wherein a length of the proximal portion of the elongate body is sufficient to form a second implanted portion.

15. The system of claim 14, further comprising a third anchor member, wherein a length of the proximal portion of the elongate body is sufficient to form a third implanted portion.

16. The system of claim 11, wherein the coating extends along an entire outer surface of the elongate body.

17. The system of claim 11, wherein the coating surrounds the distal end of the elongate body.

18. The system of claim 11, wherein the first anchor member includes a plurality of deformable flaps extending radially therefrom.

19. The device of claim 11, wherein the light fiber emits the light at the selected frequency of light so as to form the mass.

20. A device for treating a bone, comprising:
an elongate body sized and shaped for insertion into a bone and extending longitudinally from a proximal end to a distal end, the elongate body including a channel extending therethrough, the channel configured to receive a laser fiber therein, the elongate body being formed of a polymer, a distal end of the polymer including a laser absorbent material such that, when a laser emitted by the laser fiber is applied thereto, the distal end melts to form a mass;
a bone plate including an opening sized and shaped to receive the elongate body therethrough; and
an anchor member slidably mountable over the elongate body and movable therealong from a first position at the proximal end of the elongate body to a second position adjacent a bone into which the elongate body has been inserted to cooperate with the mass to fix the elongate body to the bone.

21. The device of claim 20, wherein the polymer is a thermoplastic polymer including a pigment absorbing the laser.

22. The device of claim 20, wherein the coating extends along an entire outer surface of the elongate body.

23. The system of claim 20, wherein the coating surrounds the distal end of the elongate body.

24. The system of claim 20, wherein the first anchor member includes a plurality of deformable flaps extending radially therefrom.

25. The system of claim 20, wherein the mass prevents the distal end of the elongate body from being moved proximally back into the bone.

26. The device of claim 20, further comprising a plurality of anchor members slidably mountable over the elongate body, wherein the plurality of anchor members includes the anchor member, and the anchor member is movable along the elongate body away from all others of the plurality of anchor members from the first position to the second position.

27. The device of claim 20, further comprising the laser fiber.

28. A device for treating a bone, comprising:
an elongate body sized and shaped for insertion into a bone and extending longitudinally from a proximal end to a distal end, the elongate body including a channel extending therethrough, the channel configured to receive a laser fiber therein, the elongate body being formed of a polymer, a distal end of the polymer including a laser absorbent material such that, when a laser emitted by the laser fiber is applied thereto, the distal end melts to form a mass; and
an anchor member slidably mountable over the elongate body and movable therealong from a first position at the proximal end of the elongate body to a second position adjacent a bone into which the elongate body has been inserted to cooperate with the mass to fix the elongate body to the bone,
wherein a proximal portion of the elongate body is severable from a first implanted portion extending from the distal end into the first anchor member, the device including a second anchor member, wherein a length of the proximal portion of the elongate body is sufficient to form a second implanted portion.

29. The device of claim 28, further comprising a third anchor member, wherein a length of the proximal portion of the elongate body is sufficient to form a third implanted portion.

* * * * *